US012667451B2

(12) United States Patent
Bergmann et al.

(10) Patent No.: US 12,667,451 B2
(45) Date of Patent: Jun. 30, 2026

(54) ATMOSPHERIC PRESSURE PLASMA JET DEVICE

(71) Applicant: Freiburger Medizintechnik GmbH, Freiburg (DE)

(72) Inventors: Michael Bergmann, Freiburg (DE); Loic Ledernez, Freiburg (DE); Markus Altenburger, Freiburg (DE); Samuel Liebs, Freiburg (DE)

(73) Assignee: Freiburger Medizintechnik GmbH, Freiburg (DE)

( * ) Notice: Subject to any disclaimer, the term of this patent is extended or adjusted under 35 U.S.C. 154(b) by 717 days.

(21) Appl. No.: 17/267,245

(22) PCT Filed: Aug. 7, 2019

(86) PCT No.: PCT/EP2019/071209
§ 371 (c)(1),
(2) Date: Feb. 9, 2021

(87) PCT Pub. No.: WO2020/030689
PCT Pub. Date: Feb. 13, 2020

(65) Prior Publication Data
US 2021/0161623 A1     Jun. 3, 2021

(30) Foreign Application Priority Data

Aug. 10, 2018    (EP) .................................... 18188475

(51) Int. Cl.
A61C 8/00          (2006.01)
A61L 2/14          (2006.01)
(Continued)

(52) U.S. Cl.
CPC .............. A61C 8/0013 (2013.01); A61L 2/14 (2013.01); H05H 1/42 (2013.01); H05H 1/46 (2013.01);
(Continued)

(58) Field of Classification Search
CPC ... A61C 8/0013; A61C 8/0007; A61C 8/0089; A61C 3/00; A61C 3/025; A61C 19/002;
(Continued)

(56) References Cited

U.S. PATENT DOCUMENTS 3,918,440 A * 11/1975 Kraus ...................... A61N 2/02
                                                    607/51
4,363,627 A * 12/1982 Windeler ................. A61C 5/77
                                                    433/167

(Continued)

FOREIGN PATENT DOCUMENTS

JP           2008231471 A      10/2008
WO      WO-2006048649 A1 *  5/2006   ............... H05H 1/46

OTHER PUBLICATIONS

Written Opinion and International Search Report of the International Application PCT/EP2019/071209, dated Aug. 10, 2019.

*Primary Examiner* — Edelmira Bosques
*Assistant Examiner* — Holly T. To
(74) *Attorney, Agent, or Firm* — MARSHALL, GERSTEIN & BORUN LLP; Michael P. Furmanek

(57)                    ABSTRACT

The present invention refers to an atmospheric pressure plasma jet device for disinfecting and coating a dental implant. The device comprises a gas supply and a nozzle for providing a gas to a tip of the nozzle wherein the nozzle is a single electrode nozzle having a first electrode. The device comprises further a precursor supply for providing a coating precursor to the nozzle, a second electrode and a connector for electronically connecting the second electrode with the dental implant. In another aspect the present invention refers to a system for disinfecting and coating.

17 Claims, 4 Drawing Sheets

(51) Int. Cl.
    *A61L 103/00*     (2026.01)
    *H05H 1/42*     (2006.01)
    *H05H 1/46*     (2006.01)

(52) U.S. Cl.
    CPC ....... *A61L 2103/00* (2026.01); *A61L 2202/14* (2013.01); *H05H 2245/30* (2021.05); *H05H 2245/36* (2021.05)

(58) Field of Classification Search
    CPC ......... A61L 2/14; A61L 2202/24; H05H 1/42; H05H 1/46; H05H 2245/30; H05H 2245/36
    See application file for complete search history.

(56)               References Cited

U.S. PATENT DOCUMENTS

| | | | | |
|---|---|---|---|---|
| 4,892,112 | A * | 1/1990 | Knetsch | A61C 19/002 134/102.1 |
| 5,543,019 | A * | 8/1996 | Lee | C23C 14/5806 204/192.15 |
| 5,573,732 | A * | 11/1996 | Waggener | A61L 2/14 422/907 |
| 5,588,837 | A * | 12/1996 | Rubeling | A61C 13/0003 433/172 |
| 5,645,796 | A * | 7/1997 | Caputo | A61L 2/14 422/23 |
| 5,738,521 | A * | 4/1998 | Dugot | A61C 8/0006 607/51 |
| 8,030,849 | B2 * | 10/2011 | Suslov | A61B 18/042 315/111.21 |
| 8,557,187 | B2 * | 10/2013 | Ehlbeck | A61P 17/02 422/130 |
| 8,920,361 | B2 * | 12/2014 | Staack | A61B 18/042 604/24 |
| 8,994,271 | B2 * | 3/2015 | Kindel | A61B 18/042 315/111.21 |
| 9,663,754 | B2 * | 5/2017 | Weltmann | H05H 1/42 |
| 2002/0187066 | A1 * | 12/2002 | Yu | A61L 2/14 422/23 |
| 2005/0118350 | A1 * | 6/2005 | Koulik | H05H 1/44 219/121.36 |
| 2006/0042547 | A1 * | 3/2006 | Lee | H05H 1/30 118/723 MW |
| 2009/0121638 | A1 * | 5/2009 | Price | H05H 1/46 315/111.21 |
| 2009/0142514 | A1 * | 6/2009 | O'Neill | H05H 1/46 427/595 |
| 2009/0188626 | A1 * | 7/2009 | Lu | H05H 1/2406 156/345.35 |
| 2010/0133979 | A1 * | 6/2010 | Lu | H05H 1/2406 315/111.21 |
| 2010/0273129 | A1 * | 10/2010 | Yu | A61C 5/30 433/217.1 |
| 2011/0112528 | A1 * | 5/2011 | Stieber | H05H 1/2439 606/41 |
| 2011/0116967 | A1 * | 5/2011 | Roy | H05H 1/2406 422/186.05 |
| 2011/0183284 | A1 * | 7/2011 | Yamanaka | H05H 1/2406 433/32 |
| 2012/0137635 | A1 * | 6/2012 | Qiu | B29D 11/00038 53/433 |
| 2012/0156093 | A1 * | 6/2012 | Kitano | C02F 1/4608 422/23 |
| 2012/0187841 | A1 * | 7/2012 | Kindel | H05H 1/36 315/111.21 |
| 2012/0261391 | A1 * | 10/2012 | Ihde | H05H 1/42 219/121.52 |
| 2013/0153545 | A1 * | 6/2013 | Kim | H05H 1/36 219/121.5 |
| 2014/0162206 | A1 * | 6/2014 | Ivanoff | A61N 1/325 433/32 |
| 2015/0060417 | A1 * | 3/2015 | Stehrer | H05H 1/40 219/121.48 |
| 2015/0150653 | A1 * | 6/2015 | Vladila | A61C 8/0022 433/29 |
| 2015/0282907 | A1 * | 10/2015 | Zipprich | A61C 19/063 433/32 |
| 2017/0050039 | A1 * | 2/2017 | Short | A61L 2/23 |
| 2017/0265968 | A1 * | 9/2017 | Brodbeck | A61C 17/036 |
| 2017/0339776 | A1 * | 11/2017 | Knoll | A61L 2/0011 |
| 2018/0138019 | A1 * | 5/2018 | Shindo | C01B 33/12 |
| 2019/0254734 | A1 * | 8/2019 | Konesky | A61B 18/042 |
| 2019/0269902 | A1 * | 9/2019 | Fregoso | A61C 3/03 |
| 2019/0298431 | A1 * | 10/2019 | Dai | H05H 1/466 |
| 2019/0328913 | A1 * | 10/2019 | Schlee | A61C 8/0087 |
| 2021/0069360 | A1 * | 3/2021 | Shane | A61L 2/0011 |
| 2021/0084742 | A1 * | 3/2021 | Ledernez | A61C 19/00 |
| 2021/0128280 | A1 * | 5/2021 | Gregg, II | A61C 8/0089 |
| 2021/0220669 | A1 * | 7/2021 | Morio | A61N 5/0603 |
| 2021/0405523 | A1 * | 12/2021 | Khoury | H01L 21/02115 |
| 2022/0033950 | A1 * | 2/2022 | Riemensperger | C23C 4/04 |
| 2023/0046192 | A1 * | 2/2023 | Korzec | H01J 37/32807 |
| 2023/0181780 | A1 * | 6/2023 | Hancock | H05H 1/466 422/292 |
| 2023/0269859 | A1 * | 8/2023 | Ledernez | H05H 1/3494 219/121.48 |
| 2023/0285630 | A1 * | 9/2023 | Short | A61L 26/008 424/616 |

* cited by examiner

Fig. 5

ATMOSPHERIC PRESSURE PLASMA JET DEVICE

CROSS-REFERENCE TO RELATED APPLICATION

This is the United States national phase of International Patent Application No. PCT/EP2019/071209, filed Aug. 7, 2019, which claims priority to European Patent Application No. EP18188475.0, filed Aug. 10, 2018. The entire contents of each of the foregoing applications are hereby incorporated by reference herein.

FIELD OF THE DISCLOSURE

The present disclosure relates to an atmospheric plasma jet device for disinfecting and coating a dental implant as well as a system for disinfecting and coating a dental implant.

BACKGROUND

One concept for dentures are dental implants. A secondary disease which might arise from the dental implant is peri-implantitis, an inflammatory process affecting the surrounding tissue of the dental implant. Especially gaps and cavities between the implant itself and a superstructure of the dental implant like an abutment are vulnerable for a penetration of bacteria from the oral cavity. These bacteria can cause peri-implantitis in the adjacent tissue. Conventionally, peri-implantitis is treated with antibiotics. In severe cases, the tissue attacked by the bacteria as well as the dead tissue are removed, for example, with a metal brush. During the procedure, the implant itself and the abutment are freed from the biofilm on the surface and the surface is smoothened simultaneously. However, this procedure makes an osseo-integration more difficult and the risk of a relapse remains.

GENERAL DESCRIPTION

One object of the present invention is to provide an improved device and system for treating peri-implantitis.

One aspect of the present invention includes an atmospheric pressure jet device for disinfecting and coating a dental implant. The device comprises a gas supply and a nozzle for providing gas to a tip of the nozzle. The nozzle is designed as a single electrode nozzle comprising a first electrode. The device further comprises a precursor supply for providing a coating precursor to the nozzle. The device comprises a second electrode and a connector for electronically connecting the second electrode with the dental implant.

The nozzle is designed as a single electrode nozzle in which nozzle only the first electrode is exposed to the surrounding within the nozzle but not the second electrode. The first electrode is exposed in particular to the gas channel built by the nozzle and hence to a gas from the gas supply streaming through the nozzle. In one embodiment, the second electrode or a connecting wire of the second electrode may be integrated into the nozzle but are not exposed to the surrounding, especially to the gas channel, and are hence electrically insulated.

In a second aspect of the invention the precursor supply of the plasma jet device comprises a gas wash bottle for providing a precursor in a solution or a second gas supply. The gas wash bottle may contain the liquid precursor or a solution in which the precursor is dissolved. The gas provided by the first gas supply is channeled through the gas wash bottle and enriched with the precursor. The precursor preferable contains carbon and 0.1-20% oxygen. As precursor, for example pentyl acetate or p-Xylene might be used. When having a liquid precursor, for example in form of a solution, the precursor might also be aerosolized by an ultrasonic transducer. Alternatively, the precursor might be provided in a gaseous state, for example from a second gas supply. Preferably, the precursor supply is arranged such that the precursor is supplied during operation to the gas stream from the gas supply prior to entering the nozzle.

The molecules of the precursor are activated by the plasma and can therefore be used as a coating of the dental implant. After the activation by plasma, a carbon based coating forms covalent bonds on the dental implant which are resistant against external impacts. The carbon based coating is accumulated especially on a rough surface of the dental implant and/or the abutment reducing the micro roughness. The treatment of the surface prevents or at least hinders the adhesion of bacteria. The treatment of peri-implantitis also includes a preventive treatment thereof. A preventive treatment may be performed at a previously implanted dental implant, for example, as an aftercare treatment of the implantation or as a periodic treatment. The preventive treatment may include disinfecting as well as coating.

According to a further aspect the precursor supply is activatable and de-activatable. In operation, the precursor supply can be activated and the precursor is supplied to a gas stream towards the nozzle for the process of coating. In the deactivated state of the precursor supply, the plasma jet device and the plasma itself are used for disinfection purposes only. By activating and deactivating the precursor supply between the two operating modes of the atmospheric plasma jet device, namely the first mode of disinfecting and the second mode of disinfecting and coating, might be switched. In an embodiment where the gas stream is enriched by the precursor in a gas wash bottle, the gas flow might be directed either through the gas wash bottle in the event of an activated precursor supply or otherwise passes the gas wash bottle without entering it. Instead of directing all gas through the gas wash bottle or all gas passing the gas wash bottle, gas from the gas supply might partially be directed via the gas wash bottle and partially passes the gas wash bottle such that the concentration of the precursor in the reunited gas stream might be adjusted. In an embodiment where an ultrasonic transducer is used, the transducer might be switched on and off. In a further embodiment of a gaseous precursor, a valve of the precursor supply might be opened and closed. By opening or closing the valve gradually, the concentration of the precursor in the gas stream towards the nozzle may be adjusted.

The first electrode is preferably a conductor arranged within the nozzle. The first electrode may be a substrate covering at least partially the inner surface of the nozzle. Alternatively, the first electrode may be a wire arranged coaxially within the nozzle. The first electrode may extend at least partially towards the tip of the nozzle.

According to further aspect of the invention the device is adapted to provide electrical pulses at the first electrode for producing the atmospheric pressure plasma jet at the tip of the nozzle. Therefore, a voltage generator or a function generator may be connected with the first and second electrode. The generated pulses have in one aspect at least one of the current peak value of 0.1-500 mA, an absolute voltage peak value of 100 V-100 kV and a frequency of 1 Hz-500 MHz. Preferred values for the parameters given above are 500 mA, 25000 V and 1 kHz. In one aspect the form of the pulses is one of a rectangular, parabolic, saw tooth and sinus one. In a further aspect the pulses have a duration of 10 ns.-10 ms. The pulses may be monopolar, preferably monopolar positive ones. In some embodiments, the pulses may also be bipolar pulse. For generating and adjusting the electrical parameters, the plasma jet device comprises the voltage generator or a function generator. The function generator may provide different modes including different values for said variables based on the gas and the precursor selected, the mode of disinfecting and/or coating and the design or material of the dental implant.

In one aspect of the present invention the second electrode of the plasma jet device is connected with ground. As ground earth ground may be used. In some embodiments a floating ground may be used instead. The plasma jet device is further adapted to provide electrical pulses at the first electrode for producing an atmospheric pressure plasma jet at the tip of the nozzle. The first electrode, which is arranged in the nozzle, may be exposed to the surrounding and especially to the gas channel/stream inside the nozzle. Depending on the embodiment, the exposure is set to diverse positions especially in longitudinal direction of the nozzle. Consequently, the first electrode may extend to the tip of the nozzle or end within the nozzle. The position of the bared part of the first electrode in the nozzle is one of the determinant factors where the atmospheric pressure plasma is produced during operation. Due to the gas flow towards the nozzle tip and the electrical potential between the two electrodes, a plasma jet is directed towards the tip of the nozzle and/or towards the bared second electrode. For example, when the first electrode ends in the middle of the nozzle between the first and second end and is bared at the end, plasma is produced in the middle of the nozzle and guided towards the tip of the nozzle.

The grounded second electrode which is connected to the dental implant serving as counter electrode and the plasma jet generated in the single electrode nozzle result in a directed plasma spreading and also to a directed and selective coating of the dental implant surface. The device is preferably adapted to produce in operation a low temperature atmospheric plasma between the two electrodes. Due to the directed gas stream and the directed coating process towards the second electrode and the implant, the surrounding tissue is not affected.

The gas provided by the gas supply in the operating mode of coating is a carrier gas for the precursor. The gas is in one embodiment an inert gas, preferably helium, having a relatively low ignition voltage leading to a rather homogeneous plasma and a rather high thermal conductivity. The gas flow from the gas supply may be varied, for example by the way of a valve, and is preferably between 0 and 5 I per minute.

According to one aspect of the present invention the nozzle has an outer maximum outer dimension of less than 5 mm preferably less than 1 mm. The maximum outer diameter refers in particular to the tip area of the nozzle being relevant for the treatment. The nozzle may have a circular, oval, rectangular or square shape. A flat shape may be used to insert the tip of the nozzle into a gingival pocket. The outer and/or inner dimension and/or shape may vary along the longitudinal dimension of the nozzle. The nozzle is further made of a dielectrical material, preferably of a plastic compound. In one embodiment the nozzle is made of polypropylene. The nozzle may in one embodiment be a nozzle produced in a 3D-printer.

In one aspect the connector is designed such that the distance between the first electrode and the dental implant is in use between 0.1 and 10 mm. A preferable distance is about 1 mm. Therefore, the connector is attached in such way, for example, to the nozzle that the distance between the tip of the nozzle and the dental implant is predefined to the preferred distance. In one embodiment the connector is attached to an extension of the nozzle and comprises a connecting part being adapted to engage with a bore in the implant. In another embodiment the minimum distance between the first electrode and the dental implant is defined by a spacer attachable to the nozzle.

In one aspect of the present invention the connector of the plasma jet device comprises a single or a dual contact for connecting the second electrode within the dental implant. A dual contact provides a higher reliability for the electrical connection to the dental implant and a fallback solution in case of the failure of one of the two contacts. As the plasma jet device is a medical device, a reliable connection to the dental implant, especially the implant itself, serving as counter electrode for the generation of plasma, is required.

In a further aspect the dual contact connecter may be used to detect that both contacts are connected with the implant. Therefore, one of the two electrodes serves as the second electrode and the other electrode as a third electrode, wherein the electric resistance between the second and third electrode is measured in order to detect a connection of both electrodes with the implant. As a security feature, the plasma jet may only be ignited when a contact of the second electrode with implant is detected. The connection of the third electrode may be switchable such that the third electrode may also serve as a second electrode for the plasma generation. In operation, the third electrode may be switched into second-electrode-mode or may be used alternating in second-electrode-mode and third-electrode-mode.

Generally, dental implants comprise the implant itself which is screwed into a jaw bone, i.e. the upper or the lower one, and an attachable crown. Some versions of a dental implants further comprise an abutment. In connection with the present invention it is referred to a dental implant which at least comprises the implant itself. The implant has previously been implanted into the jaw bone. Prior to connecting the connector to the implant, the crown and, if applicable, the abutment of the dental implant may be removed. The connector is then adapted to engage with the implant itself and/or the abutment.

Dental implants may further be divided into two types of implants. To one of the two implant types is referred to as screwed dental implant which comprises the implant as such to which a crown and optionally an abutment are attached by the way of a screwed connection. The second type of dental implants comprise a cemented connection between the implant itself and the crown.

The connector comprises in one aspect an external thread for a screwing connection. The screw connector is preferably used in connection with a screwed implant in such way that the connector with an external thread is screwed into the bore hole of the implant with an internal thread. The internal threads in implants generally have a diameter between 0.5 and 3 mm and a length of 2-40 mm.

According to an aspect of present invention, the connector may comprise a clamping device which is adapted to be inserted into the bore hole of the dental implant which also may be a threaded bore hole. The clamping device may have the shape of an "R" for an easy insertion into the bore hole and reliable fixation of the connector against unintentionally removal. Alternatively, the clamping device may be designed such that the clamping device engages with an external surface of the dental implant. The connector may be designed as a ring encircling the dental implant. The ring may further be secured, for example, by a clamping screw.

In a further aspect the external parts of the connector comprise an electrical insulation such that they are electrically insulated with regard to the surrounding. In this connection the oral cavity may be regarded as surrounding. The electrical insulation prohibits electrical confounding effects with regard to the ground provided to the dental implant. These confounding effects may especially occur when the patient has further metal dentures. Furthermore, the insulation helps to define the implant as counter electrode for the plasma generation and the directed plasma jet towards the implant. Therefore, preferably the surfaces of the screw head which are averted to the dental implant are covered with an insulation. Additionally, the wire of the second electrode connected with the screw of the connector may also be electrically insulated.

A second aspect of the present invention is a system for disinfecting and coating comprising a plasma jet device as described above and a dental implant.

According to one aspect of the present invention the implant itself and/or the abutment of the dental implant consists of metal or a ceramic material. In order the implant serving as a counter electrode, the implant must have an electric conductivity. A ceramic implant may comprise therefore metal additives. Electrically conductive ceramic materials are, for example, metal-like carbides or nitrides like silicon carbide, boron carbide or titanium suboxide. Metal implants preferably consist of titanium or a titanium based alloy.

A third aspect of the present invention is a method of disinfecting and/or coating a dental implant. Therefore, the dental implant, preferably the implant itself, is connected via a connector with a second electrode. In addition, a nozzle for providing a gas to a tip of the nozzle is provided wherein the nozzle is a single electrode nozzle comprising a first electrode. The gas is directed, optionally together with a precursor, towards the tip of the nozzle. Additionally, an electrical field between the nozzle and the dental implant is provided for generating the atmospheric pressure plasma at the tip of the first electrode. Preferably, the electrical field is provided by generating pulses at the first electrode. The method further comprises the generation of a plasma jet towards the counter electrode preferably towards the dental implant. The method is preferably conducted with a device or a system described in connection with the present invention.

BRIEF DESCRIPTION OF THE DRAWINGS

Preferred embodiments of the present invention are described by the way of example only, with reference to the accompanying drawings in which:

FIG. 5 shows a sectional view of a second alternative of a screw connector for connecting the second electrode with a dental implant.

DETAILED DESCRIPTION

Figure 1:
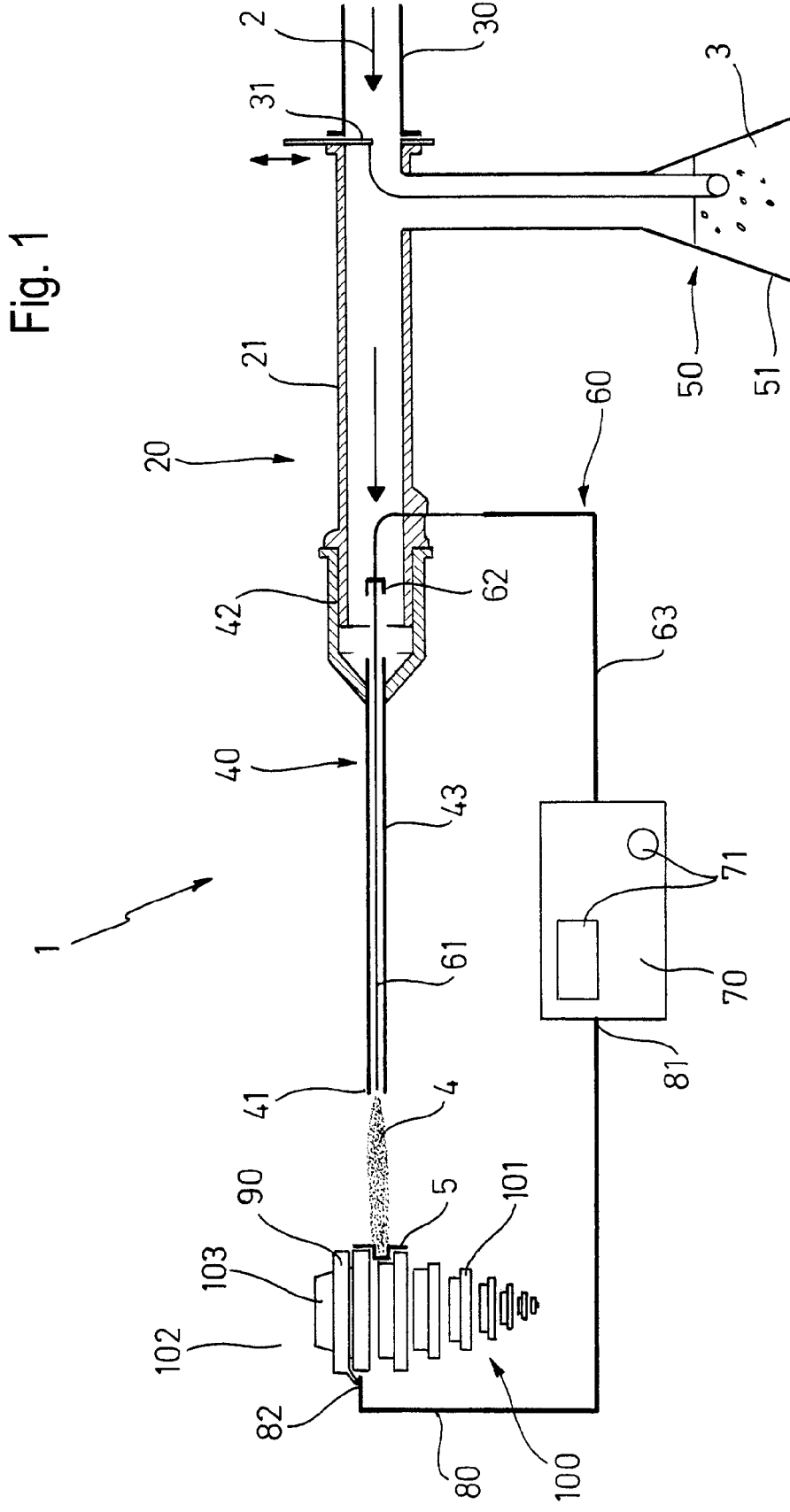
FIG. 1 shows a schematic arrangement of a system comprising a plasma jet device for disinfecting and coating a dental implant and a dental implant, FIG. 2a, b show two alternative electric connections between the dental implant and the second electrode.

FIG. 1 shows a schematic arrangement of a system for disinfecting and coating a dental implant 1 with an atmospheric pressure plasma jet device 20. The atmospheric pressure plasma jet device 20 comprises a gas supply 30 and a nozzle 40, wherein a device body 21 connects the gas supply 30 with the nozzle 40. The gas supply 30 comprises a tank as a gas reservoir (not shown) for providing a predefined pressure and flow rate of gas 2 to device body 21 and further the nozzle 40. The plasma jet device 20 further comprises a precursor supply 50 in form of a gas wash bottle 51. The gas wash bottle 51 is connected to the device body 21. The gas 2 provided by the gas supply 30 can be directed through the gas wash bottle 51 where it is enriched with a precursor 3. The gas 2 is directed via the gas wash bottle 51 during the process of coating. Therefore, a spool valve 31 is set to a first position in which the gas 2 is directed completely to the gas wash bottle 51 as shown in FIG. 1. In a second position which is not shown, the overflow orifice to the gas was bottle 51 in the valve 31 is closed and the gas 2 is supplied directly to the nozzle without being redirected via the gas wash bottle 51. In this position, the plasma jet device 20 is in the operating mode of disinfecting only without coating. The spool valve may be also set to intermediate positions between the first and second position The nozzle 40 in the shown embodiment has the basic shape of a cylindrical tube. At a first end, the tip 41 is providing an exit opening for the gas 2 and/or the plasma 4 generated. At the opposite end, the nozzle 40 comprises a connecting portion 42 for connecting the nozzle 40 with a plasma jet device body 21. The nozzle 40 comprises a tubular nozzle portion 43 between the nozzle tip 41 and the connecting portion 42. The tubular nozzle portion 43 consists in one embodiment of a plastic body made of polypropylene.

Inside the nozzle 40 is a nozzle portion 61 of the first electrode 60 arranged. The nozzle portion 61 is a wire which is arranged coaxially in the tubular nozzle portion 43. In the shown embodiment the nozzle portion 61 extends into the tip area of the nozzle 40. On the opposite end, the nozzle portion 61 engages with an electrode connector 62 for connecting a nozzle portion of the first electrode 61 with a wiring 63 leading to a base station 70.

The base station 70 comprises a function generator inside and I/O devices 71 for selecting and monitoring different operating modes. The base station 70 is further connected to a first end 81 of a second electrode 80. An opposite second end 82 of the second electrode 80 is connected to a connector 90 for connecting the second electrode 80 with a dental implant 100. The connector 90 is designed as a ring encircling an abutment 103 of a dental implant 100. The dental implant 100 further comprises the implant 101 itself, which has previously been implanted into the jaw bone, and a crown 102.

Figure 2A:
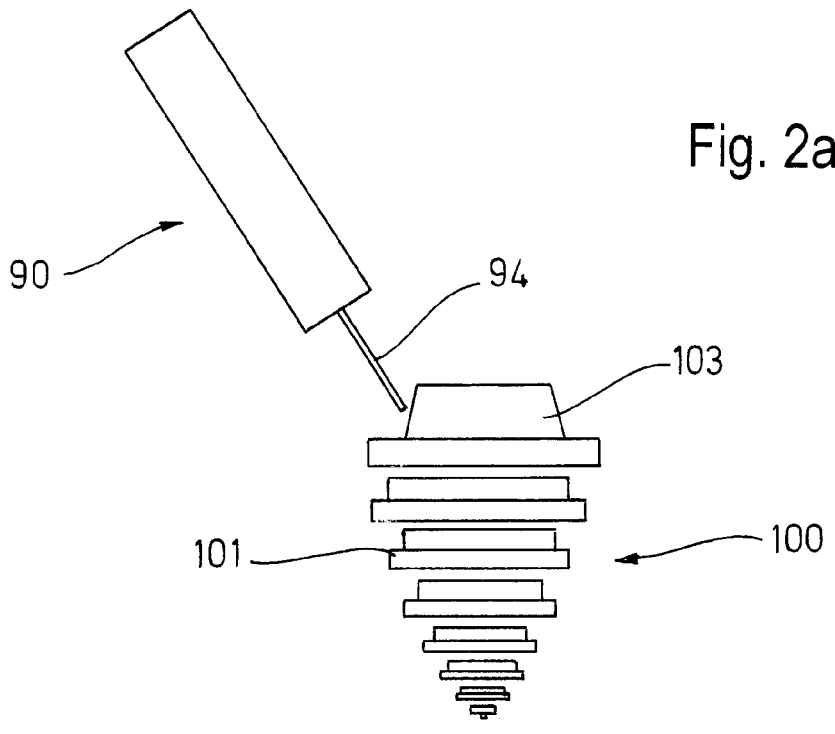

FIGS. 2a and b show two different kinds of electrical contact between the second electrode 80 and the connector 90 respectively and the dental implant 100 with the implant 101 and the abutment 103. In FIG. 2a the second electrode 80 is connected in a single contact 94 via the connector 90 to the implant 100 in form of a metal implant.

Figure 2B:
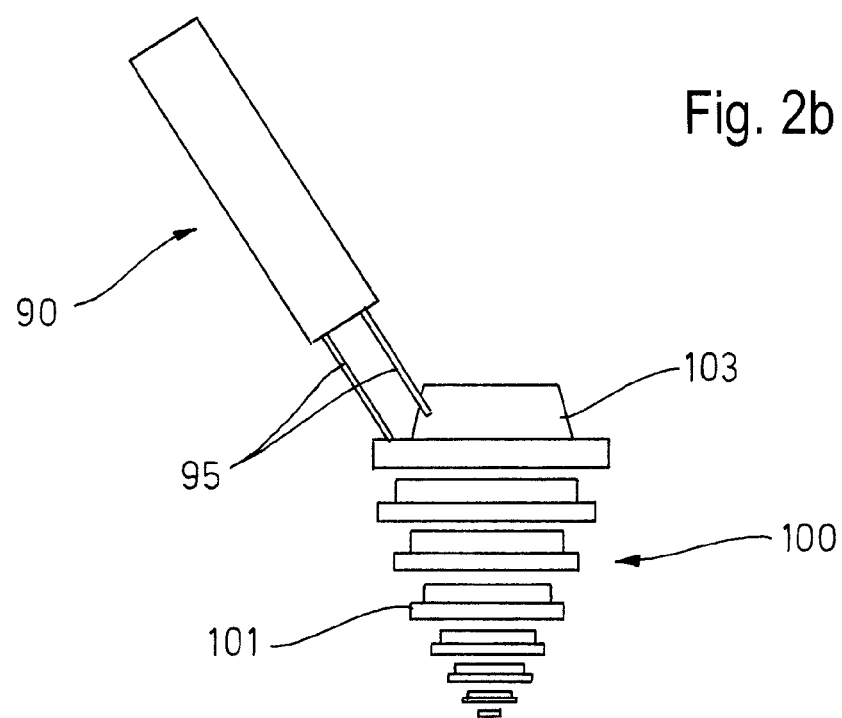

The connector 90 shown in FIG. 2b is designed as a dual contact connector. Such a connector 90 with a dual contact 95 may be used in order to reliably connect the second electrode 80 with the implant 100 in order to generate low temperature atmospheric pressure plasma.

Figure 3:
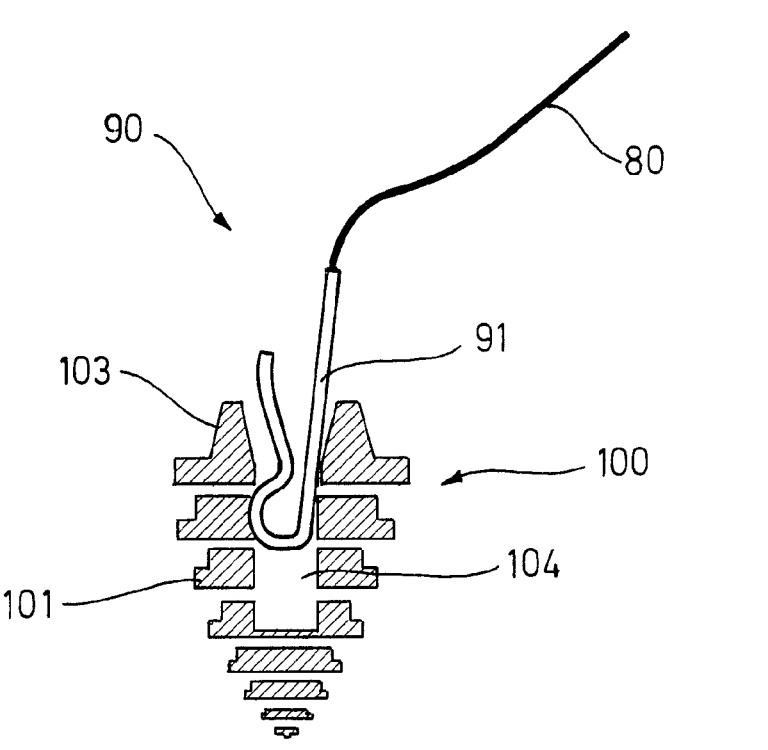
FIG. 3 shows a sectional view of a clamping connector connecting the second electrode with the dental implant.

FIG. 3 shows a sectional view of a first embodiment of a connector 90. The dental implant 100 comprises the implant 101 and an abutment 103 being connectable to a crown 102 (not shown) via a screwed connection. Such a dental implant 100 usually contains a blind bore 104 with an inner thread. A clamping device 91 is inserted into the blind bore 104. In the shown embodiment, the clamping device 91 has an R-shape to securely connect the dental implant 100 with the second electrode 80.

Figure 4:
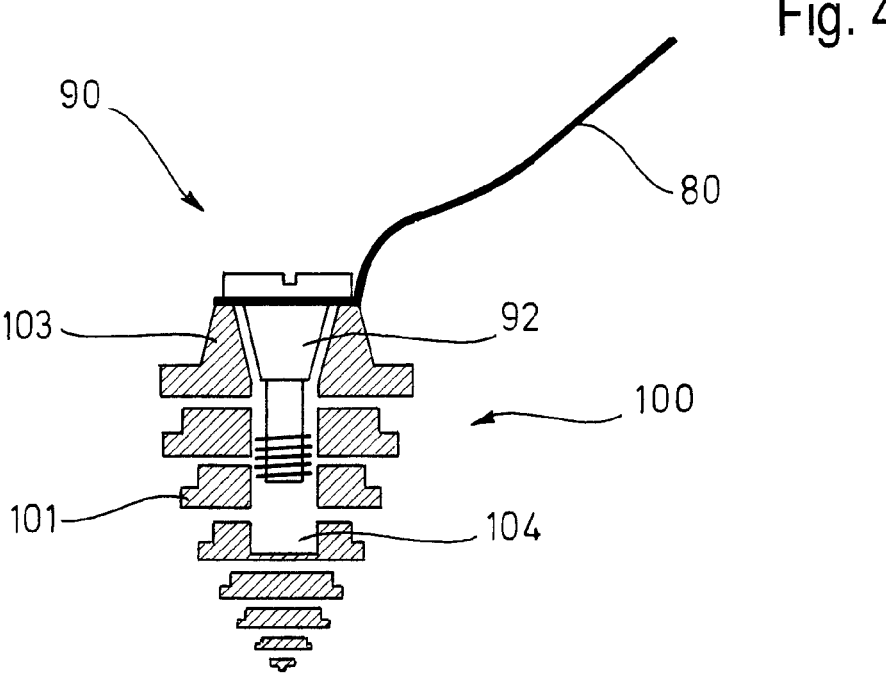
FIG. 4 shows a sectional view of a first alternative of a screw connector for connecting the second electrode with the dental implant.

In an alternative embodiment shown in FIG. 4 in a sectional view the connector 90 comprises a screw 92. The screw 92 fits into the blind bore 104 and can be screwed into the inner thread of the blind bore 104. The second electrode 80 is connected rotatably with the screw 92 in the area of screw head. In the shown embodiment the second electrode 80 is clamped between the screw head and the dental implant 100.

Figure 5:
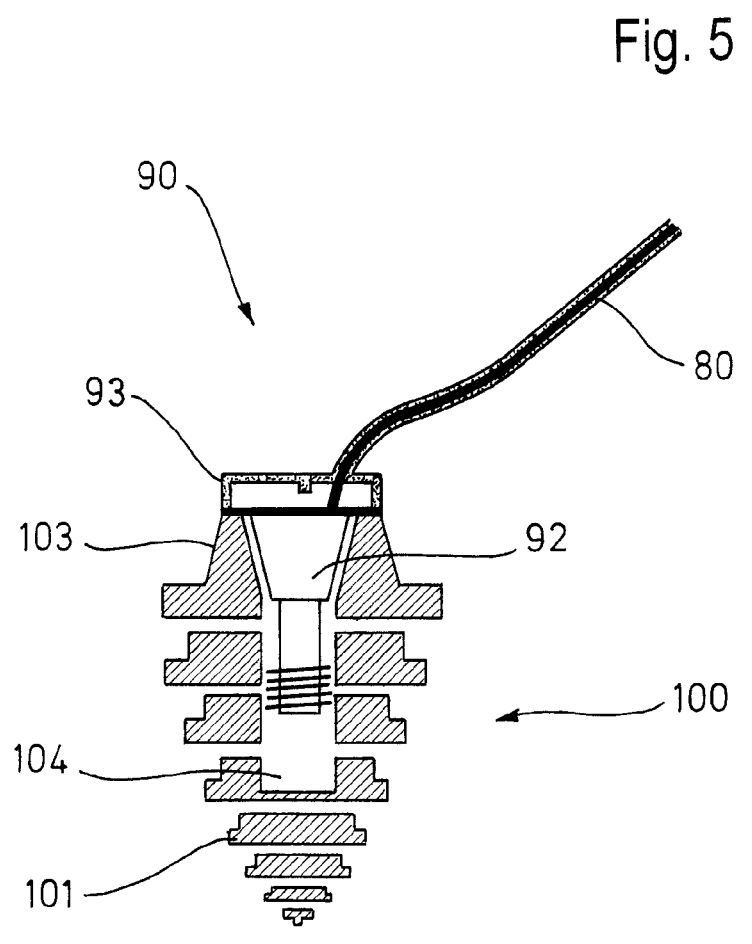

FIG. 5 shows a sectional view of a further embodiment of a screwed connection between the connector 90 and the dental implant 100. The embodiment differs from the embodiment shown in FIG. 4 in that the connector 90 and the second electrode 80 contain an insulation 93. The insulation 93 covers the exposed areas of the head of the screw 92 and the second electrode 80.

The invention claimed is:

1. An atmospheric pressure plasma jet device for disinfecting and coating a dental implant comprising
  a gas supply and a nozzle for providing a gas to a tip of the nozzle wherein the nozzle is of a single-electrode type having a first electrode with an exposed end portion disposed within the nozzle,
  a precursor supply for providing a coating precursor to the nozzle,
  a second electrode and a connector for electronically connecting the second electrode with the dental implant for the dental implant to serve as counter electrode for the generation of plasma, such that the plasma is generated by an electric field between the exposed end portion of the first electrode and the counter electrode, and that the plasma is a directed plasma jet towards the implant.

2. The plasma jet device according to claim 1, wherein the precursor supply comprises a gas wash bottle for providing the precursor in a solution or a second gas supply and/or wherein the precursor supply is activatable.

3. The plasma jet device according to claim 1, wherein the first electrode is a conductor arranged within the nozzle.

4. The plasma jet device according to claim 1, being adapted to provide electrical pulses at the first electrode for producing the atmospheric pressure plasma jet at the tip of the nozzle.

5. The plasma jet device according to claim 1, wherein pulses at the first electrode have at least one of a current peak value of 0.1 to 500 mA, and a frequency of 1 Hz to 500 MHz.

6. The plasma jet device according to claim 1, wherein pulses at the first electrode are one of a rectangular, parabolic, saw tooth or a sinus shape and/or have a pulse duration of 10 ns to 10 ms and/or are monopolar.

7. The plasma jet device according to claim 1, wherein the second electrode is connected with ground.

8. The plasma jet device according to claim 1, wherein a maximum outer dimension of the nozzle is less than 5 mm and/or wherein the nozzle is made of a plastic.

9. The plasma jet device according to claim 1, wherein the connector is designed such that a distance in use between the first electrode and the dental implant is between 0.1 and 10 mm.

10. The plasma jet device according to claim 1, wherein the connector comprises a single or dual contact for connecting the second electrode with the dental implant.

11. The plasma jet device according to claim 1, wherein the connector comprises a screwing connection for connecting the connector with the dental implant and/or wherein the external parts of the connector comprise an electrical insulation.

12. The plasma jet device according to claim 1, wherein the connector comprises a clamping device adapted to be inserted into bore hole of the dental implant.

13. A system for disinfecting and coating comprising a plasma jet device according to claim 1 and a dental implant.

14. The system according to claim 13 wherein the dental implant comprises an implant itself and an abutment wherein the connector is adapted to engage with the implant itself and/or the abutment.

15. The system according to claim 14, wherein the implant itself and/or the abutment are made of metal or a ceramic material.

16. The plasma jet device according to claim 1, wherein the exposed end portion of the first electrode is arranged in the tip of the nozzle.

17. The plasma jet device according to claim 1, wherein pulses at the first electrode have a peak value of 100V to 2500V.

* * * * *